United States Patent [19]

Palinczar

[11] Patent Number: 4,686,099

[45] Date of Patent: Aug. 11, 1987

[54] AEROSOL WATERPROOF SUNSCREEN COMPOSITIONS

[76] Inventor: Victor Palinczar, 435 Adeline St., Trenton, N.J. 08611

[21] Appl. No.: 807,488

[22] Filed: Dec. 10, 1985

[51] Int. Cl.$^4$ .......................... A61K 7/42; A61K 7/44; A61K 9/12

[52] U.S. Cl. ........................................ 424/47; 424/59; 424/60

[58] Field of Search .............................. 424/59, 60, 47

[56] References Cited

U.S. PATENT DOCUMENTS

| | | | |
|---|---|---|---|
| 3,184,388 | 5/1965 | Kalopissis et al. | 424/47 |
| 3,210,251 | 10/1965 | Klug | 424/47 |
| 3,696,193 | 10/1972 | Guglielmetti | 424/47 X |
| 3,836,665 | 9/1974 | Eberhardt | 424/47 |
| 3,895,104 | 7/1975 | Karg | 424/47 |
| 3,970,584 | 7/1976 | Hart et al. | 424/47 |
| 4,002,733 | 1/1977 | Degen et al. | 424/47 |
| 4,045,549 | 8/1977 | Gerecht | 424/47 |
| 4,193,989 | 3/1980 | Teng et al. | 424/60 |
| 4,254,102 | 3/1981 | Kaplan et al. | 514/561 |
| 4,567,038 | 1/1986 | Ciaudelli et al. | 424/60 |

*Primary Examiner*—Dale R. Ore
*Attorney, Agent, or Firm*—Sachs & Sachs

[57] ABSTRACT

An effective, aesthetic water-proof aerosol sunscreen composition which provides ultraviolet light protection to the skin includes monohydric alcohols in an amount from 20% up to about 90% by weight, from about 1% to about 20% by weight of an active suncreen agent, from about 0.1% to about 5.0% by weight of ethyl cellulose and from about 10% to about 75% of liquified propellant.

Composition may optionally contain up to about 35% by weight of volatile liquid carriers; up to about 20% by weight of water-insoluble emollients and up to about 3% of fragrance oil.

21 Claims, No Drawings

AEROSOL WATERPROOF SUNSCREEN COMPOSITIONS

BACKGROUND OF THE INVENTION

1. Field of the Invention

This invention relates to novel sunscreen compositions which, when applied to the human skin provide protection against the harmful effects caused by ultraviolet radiation. More particularly, this invention relates to sunscreen compositions in the form of aerosols wherein an ultraviolet light-absorbing ingredient is sprayed on the skin and is provided with increased water resistant characteristics with the aid of a polymeric binder. Most particularly, this invention relates to sunscreen compositions that are water proof and fulfill the guidelines established by the Food and Drug Administration, as listed in the Federal Register Volume 43, Number 166.

2. Discussion of the Relevant Art

Sunscreen compositions are commonly used during outdoor activity. Many people have occupations which require them to be exposed to the sun for long periods of time. Others choose to use their free time in outdoor recreations e.g. sunbathing, playing golf, surfing, fishing, skiing and swimming. All of these activities promote perspiration or allow the body to come in contact with water. Numerous sunscreen compositions have been developed which absorb ultraviolet light in a region of 280 to 320 nanometers (2800-3200 Angstroms; referred to as the "erythemal region") to protect the human body against this radiation that produces erythema and skin cancer, whether the source be from the sun or from man made devices. These compositions also incorporate ultraviolet absorbing agents that absorb in the region between 320 and 380 nanometers (3200-3800 Angstroms) and should be resistant to removal from the skin by perspiration or water in order to broaden and prolong their effectiveness.

Numerous substantive sunscreen agents, and substantive and water-resistant sunscreen compositions are available today. Development of substantive sunscreen agents and sunscreen compositions containing these substantive agents are illustrated in U.S. Pat. Nos. 3,864,473 issued to Cicendelli; 4,004,074 issued to Gerecht; and 4,256,664 issued to Epstein. These compositions make use of sunscreen agents that are not approved by the FDA and their topical use is limited.

No known sunscreen agent, that achieves a degree of water-resistancy, has been approved by the Food and Drug Administration. FDA approved sunscreen agents have, however, been incorporated into compositions which upon application to the skin physically keep the sunscreen agent on the skin during perspiration or immersion in water. The majority of these compositions make use of polymeric materials that are either emulsified in the composition or carried to the skin by a vehicle in which a continuous polymeric film is cast on the skin.

The use of an acid form of a cross-linked co-polymer of ethylene-maleic anhydride composition in the form of a gel is illustrated in U.S. Pat. No. 3,821,363 issued to Black. Compositions and methods are described in U.S. Pat. No. 3,895,104 issued to Karg in which polyamide resinous material is used as a film former. The use of acrylate/acrylic acid co-polymer compositions in the form of oils and emulsions are illustrated in U.S. Pat. No. 4,172,122 issued to Kubik. In U.S. Pat. No. 4,254,102 issued to Kaplan there is described the use of compositions containing hydroxyethyl-cellulose in conjunction with a surface active agent and a fatty alcohol. In U.S. Pat. No. 4,193,989 issued to Teng, there is described gel compositions of hydroxypropyl cellulose acetate as the film former.

Known compositions that make use of polymers to form a continuous polymeric film in which the active sunscreen agent is homogeneously dispersed throughout the matrix of the film have numerous disadvantages. Aqueous based compositions in which the polymer is usually emulsified have long drying rates on the skin, foam on the skin during application and during the drying cycle leave the skin feeling tacky. These compositions, if not fully dried, also have a tendency to allow particulate matter, such as beach sand, to adhere to the skin. Furthermore, the water-resistant properties of these aqueous based compositions are decreased if they are not fully dried before perspiration or entry into water. The formation of a continuous protective film on the skin is prevented by compositions which make use of solvent systems because they cannot tolerate large amounts of oil and other emollients. Without the use of emollients in compositions containing alcohols, the skin may become dry and irritated. Generally these compositions are also formulated in thin solutions with low viscosities which make them difficult to apply to the skin in an even manner.

Compositions, which make use of an ethylcellulose polymer, in combination with ethanol as a solvent and are effective in resisting water wash off, are products currently marketed by Carter-Wallace, Inc., New York, N.Y. under the trade names of BLOCK OUT and SEA & SKI. These compositions, however, are low in viscosity, contain high levels of silicone fluids and are costly to produce. They are also difficult to apply to the skin evenly thus permitting spot burning to occur, which may result in extreme pain and blistering of the skin. This effect is more pronounced with individuals having fair complexions and who normally use sunscreen products having high SPF (Sun Protection Factor) values. Water-resistant compositions described heretofore or that are currently being marketed in addition to being difficult to apply to the skin evenly, must be applied by using the hand. This limits the application of the product to areas where only the hands can reach, leaving a void on certain areas of the back. Furthermore, the constant accumulation of sand on ones hands while at the beach makes it unappealing to apply the sunscreen by hand.

The present invention overcomes the shortcomings of known water-resistant sunscreen compositions that make use of polymer-solvent systems, and sunscreen compositions that make use of ethylcellulose in combination with high levels of silicone fluids, by incorporating ingredients that resist removal of the active sunscreen agent by perspiration and water applied to the skin. The present invention, allows the composition to be applied to the skin evenly and easily to all parts of the body without using ones hands and without using high levels of emollients, such as silicone fluids, that protect the skin from the harmful effects of the sun's radiation. There is a need for such a product for both health and cosmetic reasons. Ingredients may be available which exhibit one or more of these desired attributes. However, the combination of these attributes for use in preparing water-proof sunscreen systems has not been demonstrated. Ingredients that have not been used previous to this invention in water-proof sunscreen compositions for fulfilling these requirements are the combination of active sunscreen agents, ethyl cellulose polymer, monohydric alcohols and liquified propellants.

SUMMARY OF INVENTION

This invention relates to very effective, highly aesthetic water-proof aerosol sunscreen compositions which provide ultraviolet light protection to the skin comprising monohydric alcohols in an amount from 20% up to about 90% by weight, from about 1% to about 20% by weight of an active sunscreen agent, from about 0.1% to about 5.0% by weight of ethylcellulose and from about 10% to about 75% of liquified propellant.

The compositions may optionally contain up to about 35% by weight of volatile liquid carriers; up to about 20% by weight of water-insoluble emollients and up to about 3% by weight of fragrance oil.

DESCRIPTION OF THE PREFERRED EMBODIMENTS

It has been discovered that highly effective, non-irritating, cosmetically aesthetic water-proof aerosol sunscreen compositions containing monohydric alcohols, such as, ethanol or isopropanol, a polymeric film former, such as, ethylcellulose, active sunscreen agents, and liquified propellants are prepared by solubilizing the ethylcellulose in the monohydric alcohol, and then adding the active sunscreen agent. Upon complete dissolution of the sunscreen agent, the mixture is placed in a conventional aerosol container and the desired amount of liquified propellant is added. The aerosol spray valve may be crimped on the aerosol container before or after the addition of the liquified propellant.

It has also been discovered that the composition may contain volatile liquid carriers for the purpose of adjusting the rate of evaporization of the monohydric alcohol and to control the rate of film formation of the ethylcellulose on the skin. It has further been discovered that the compositions may additionally contain water-insoluble emollients which serve to prevent the skin from drying, leaving the skin feeling smooth and soft.

It has additionally been discovered that the ethylcellulose although having a propensity for oxygenated organic compounds has a greater tolerance with non-polar compounds than other polymers which are soluble in monohydric alcohols. This compatibility allows for a broad range in the overall solubility parameter of the composition. Such a range in the solubility parameter allows the composition to contain high levels of non-polar ingredients such as isoparaffins, isobutane and methyl phenyl polysiloxanes. Most important, is the compatibility with the non-polar liquified propellants. In addition to these ingredients the compositions may additionally contain fragrance oil. These ingredients are more specifically described below.

While not wishing to be limited by any theory of the mechanism of the activity of the invention, it is believed that the use of ethylcellulose is very important in maintaining both the degree of water resistance and the ability to be compatible with a variety of ingredients to form a continuous film of the compositions mentioned herein on the skin.

When the water-proof composition of the present invention is sprayed on the skin the application feels cool and soothing. The monohydric alcohol and liquified propellants, which are usually a major constituent of the compositions, evaporate from the skin leaving a water-insoluble flexible film consisting of a high ratio of active sunscreen agents to organic and inert ingredients. The water-insoluble film also helps prevent the loss of the active sunscreen agents by physical abrasion and is unaffected by bodily salts expelled from the body during perspiration. It is believed that the ethylcellulose film allows perspiration to pass through the continuous film in the vapor state, thereby leaving the film intact and continuous. It is further believed that the ethyl cellulose film, in addition to containing the active sunscreen agent at a high ratio of sunscreen agent to ethyl cellulose, prevents the migration of the active sunscreen agent from the matrix of the film keeping the active sunscreen agent on the surface of the skin, thereby decreasing percutaneous absorption through the skin of the active sunscreen agent. It is therefore believed that the combination of these actions cause these compositions to be effective for long periods of time and to resist removal by water and perspiration.

MONOHYDRIC ALCOHOLS

Monohydric alcohols, for example, those having about 2-8 carbon atoms such as ethanol or isopropanol are the preferred alcohols used in this composition. The present composition may contain up to about 90% of monohydric alcohols. The preferred amount of the monohydric alcohol is from about 25% to about 65% and most preferably from about 35% to about 55%. Amounts of less than about 25% are also acceptable if used in combination with ingredients that allow the ethyl cellulose polymer to remain in solution.

It will be understood that if one replaces any portion of the monohydric alcohol, with one ingredient or a mixture of ingredients that do not have rates of evaporation and viscosity similar to that of the monohydric alcohol, compositions prepared with these ingredients or a mixture of these ingredients, will have their drying rates, water-resistancy sun protection factor, and overall cosmetic aesthetics reduced. It will be further understood that the monohydric alcohols provide excellent compatibility with an array of cosmetically acceptable ingredients, and any ingredient combination may be made without departing from this spirit and scope of this invention.

THE POLYMERIC FILM-FORMER

Polymers, such as the ETHOCELS manufactured by (The Dow Chemical Company, Midland, Mich.) are derivatives of cellulose in which the anhydroglucose unit is substituted with an ethoxyl group having a softening point at about 130 degrees C. to about 170 degrees C.; a melting point at about 160 degrees C. to about 220 degrees C. These polymers are further described by the degree of substitution of the anhydroglucose unit, which contains three reactive hydroxyl sites. Substitution of all hydroxyl groups with ethoxyl groups would have a degree of substitution of 3. If half of the anhydroglucose unit of the polymer were substituted with three ethoxyl groups and the other half were substituted with two ethoxyl groups, leaving one unsubstituted hydroxyl group on every other anhydroglucose unit, the ethylcellulose would have a degree of substitution of 2.5. The difference in physical properties of ethylcellulose results from variation in the degree of etherification. Ethylcellulose containing 2.25 to 2.58 ethoxyl groups per anhydroglucose units are further referred to by ethoxyl content of 45% to 49.5%, respectively. The polymers of ethylcellulose are further described by different viscosities in which the length of the polymer's molecule increases. The preferred polymers of ethylcellulose are those polymers having an ethoxyl content between 48% to about 49.5% and are sold under the trade name (ETHOCEL "Standard" ethoxy) having a viscosity designation between 4 and 200. The present invention may contain from about 0.1% to about 5% by weight of these ethylcellulose polymers or a mixture thereof. The preferred amount of ethylcellulose polymer is from about 0.5% to about 2% by weight of the total composition. The chemical composition of polymers, especially those derived from cellulose is highly complex and usually contain a broad spectrum of molecular weight species. For this reason applicant wishes not to be limited solely to the ethylcellulose polymers mentioned in the present invention.

THE ACTIVE SUNSCREEN AGENT

Any active sunscreen agent, capable of absorbing the harmful effects of ultraviolet radiation which is, non-irritating, non-toxic and is compatible with the ingredients used in the composition and which, when applied to the skin, are homogeneously dispersed throughout the film formed by the ethylcellulose polymer, can be used. Active sunscreen agents that meet these criteria are: PABA (para-aminobenzoic acid); Cinoxate (2-ethoxyethyl p-methoxycinnamate); diethanolamine p-methoxycinnamate; digalloyl trioleate; Dioxybenzone (2,2'-dihydroxy-4-methoxybenzophenone); ethyl 4-(bis(hydroxyprcpyl))aminobenzoate; 2-ethylhexyl 2-cyano-3,3-diphenylacrylate; ethylhexyl p-methoxycinnamate; 2-ethylhexyl salicylate; glyceryl aminobenzoate; Homosalate (3,3,5-trimethylcyclohexyl salicylate); menthyl anthranilate (menthyl o-aminobenzoate); Oxybenzone (2-hydroxy-4-methoxybenzophenone); Padimate A (amyl p-dimethylaminobenzoate); Padimate O (octyl p-dimethylaminobenzoate); 2 phenybenzimidazole-5-sulfonic acid; Sulisobenzone (5-benzoyl-4-hydroxy-2-methoxybenzenesulfonic acid); triethanolamine salicylate; 4-tert.butyl-4-methoxy-dibenzoylmethane; and benzalphthalide.

The present invention may contain from about 1% to about 25% by weight of these active sunscreen agents or a mixture thereof. The preferred total amount of the active sunscreen agent is dependent upon the SPF value (Sun Protection Factor) desired to be obtained. The preferred sunscreen agents in the present invention are Padimate 0 in amounts from about 2% to about 10% by weight; Padimate A in amounts from about 1% to about 8% by weight; 2-ethylhexyl salicylate in amounts from about 3% to about 8% by weight; ethyhexyl p-methoxycinnamate in amounts from about 2% to about 8% by weight, Dioxybenzone from about 1% to about 5% by weight and Oxybenzone from about 1% to about 7% by weight.

THE PROPELLANT

Any liquified propellant, capable of producing a sufficient vapor pressure for expelling the composition from a conventional aerosol container which, is non-irritating, non-toxic and is compatible with the ingredients used in the composition and when applied to the skin allows the formation of a continuous polymer film in which the active sunscreen agent is homogeneously dispersed, can be used. Propellants that meet these criteria are: butane; isobutane; propane; dimethyl ether; dichlorodifluoromethane; tetrafluoromethane; dichlorotetrafluoroethane; chlorodifluoromethane; chlorodifluoroethane; and difluoroethane. The preferred propellants of the present invention are isobutane and propane. The present composition may contain from about 10% to about 75% of liquified propellants. The preferred amount of liquified propellant is from about 20% to about 50%.

VOLATILE LIQUID CARRIER

The present composition may also contain, as an optional ingredient, from about 0% to about 35% by weight of a volatile liquid carrier. Such liquids are in the liquid state at room temperature (about 22 degrees C.) and evaporate completely from the skin within thirty minutes after spraying the composition of the present invention onto the body. From these liquids a group of liquids have been selected which are organic in nature having a low degree of irritation and toxicity, that are generally considered safe for topical use, that provide for a controlled rate of evaporation of the monohydric alcohols used in the present composition, that allow for the formation of a continuous polymeric film of ethylcellulose and active sunscreen agents are hereinafter referred to as volatile liquid carriers of the present composition. Preferred volatile liquid carriers include but are not limited to dimethyl succinate, trichlorofluoromethane; and $C_{10}$–$C_{16}$ isoparaffins. The most preferred volatile liquid carriers are $C_{12}$–$C_{14}$ isoparaffins and dimethyl succinate. The preferred amount of the volatile liquid carrier is from about 5% to about 20% by weight.

THE WATER-INSOLUBLE EMOLLIENT

The present composition may additionally contain, as an optional ingredient, from about 0% to about 20% by weight of water-insoluble materials that are usually in the liquid state at room temperature (about 22 degrees C.) and have a water solubility of less than about 1% at 25 degrees C. From these liquids a group of liquids have been selected which are organic in nature having a low degree of irritation and toxicity, that are generally considered safe for topical use, that provide a softening or soothing effect on surface skin tissue and are hereinafter referred to as the water-insoluble liquid emollients in the present composition.

Preferred water-insoluble liquid emollients include fatty acids such as oleic and recinoleic; fatty alcohols such as oleyl, lauryl, and hexadecyl (ENJAY); esters such as diisopropyl adipate, benzoic acid esters of $C_9$–$C_{15}$ alcohols, and isononyl iso-nonanoate; alkanes such as mineral oil; alkenes such as polybutenes; silicones; such as dimethylpolysiloxane and methyl phenyl polysiloxane and ethers such as polyoxypropylene butyl ethers and polyoxpropylene cetyl ethers. The most preferred water-insoluble liquid emollients are: polybutene 30 cst., methyl phenyl polysiloxane, dimethylpolysiloxane 5.0 cst. and polyoxypropylene (14) butyl ether. The preferred amount of water-insoluble liquid emollient is form about 2% to about 15% by weight, preferably from about 4% to about 10%.

The water-insoluble liquid emollient can be used to decrease any drying effect to the skin attributed by the monohydric alcohol and also to control the rate of product depositing on the skin. One skilled in the art will easily be able to adjust the cosmetic aesthetics and physical characteristics of the composition by combining various amounts of suitable water-insoluble liquid emollients.

The waterproof aerosol sunscreen composition of the present invention may be made in a variety of ways known to those skilled in the art. In one procedure, the monohydric alcohol and the ethylcellulose polymer are heated to about 60 degrees C. in a vessel with agitation. When dissolution is complete, the active sunscreen agent is mixed until a complete solution is formed. The optional ingredients may then be added or the mixture may be allowed to cool to room temperature. The solution is then filtered through a micro-filtering system and placed into a suitable aerosol container. The headspace in the aerosol container is removed by vacuum and a commercially available aerosol valve is crimped onto the container. Propellant is then placed into the container either through the valve stem or around the stem.

Another procedure for preparing aerosol sunscreen compositions of the present invention would be to combine all the required ingredients desired in the compositions in a suitable vessel and mix until a complete solution is formed. Head pressure is placed on the mixing vessel. The composition is filtered in-line and is filled into suitable aerosol containers which were previously vacuumized and crimped with an aerosol valve.

The following formulation examples are given to further illustrate the present invention. It is to be understood, however, that the invention is not limited thereto. The formulation examples were sprayed on the skin and allowed to dry for fifteen minutes. They were then tested using the prescribed water resistancy test method described in the Federal Register Volume 43, number 166, and were considered to be resistant to removal from the skin by water and perspiration while maintaining their dry SPF value for periods of up to 80 minutes.

EXAMPLE 1

| INGREDIENTS | PERCENT BY WEIGHT |
| --- | --- |
| Ethanol | 55.8 |
| Padimate O | 8.0 |
| Ethylcellulose STD 100 vis. | 1.2 |
| Isobutane | 35.0 |
| | 100.0 |

EXAMPLE 2

| Ingredients | PERCENT BY WEIGHT |
| --- | --- |
| Ethanol | 63.8 |
| Ethyl 4-bis(hydroxypropyl) aminobenzoate | 5.0 |
| Ethylcellulose STD 100 vs. | 1.2 |
| Isobutane | 25.0 |
| Propane | 5.0 |
| | 100.0 |

EXAMPLE 3

| INGREDIENTS | PERCENT BY WEIGHT |
| --- | --- |
| Ethylhexyl p-methoxycinnamate | 7.5 |
| Isopropanol | 10.0 |
| Ethanol | 44.0 |
| Ethylcellulose STD 45 | 1.5 |
| Polybutene 30 CST | 2.0 |
| Trichlorofluoromethane | 5.0 |
| Isobutane | 25.0 |
| Propane | 5.0 |
| | 100.0 |

EXAMPLE 4

| INGREDIENTS | PERCENT BY WEIGHT |
| --- | --- |
| Ethanol | 28.0 |
| Padimate O | 8.0 |
| Dioxybenzone | 3.0 |
| Ethylcellulose STD 200 | 1.0 |
| $C_{12}$–$C_{14}$ Isoparaffin | 10.0 |
| Trichlorofluoromethane | 20.0 |
| Dichlorodifluoromethane | 30.0 |
| | 100.0 |

EXAMPLE 5

| INGREDIENTS | PERCENT BY WEIGHT |
| --- | --- |
| Ethanol | 43.0 |
| Padimate O | 8.0 |
| Dimethyl succinate | 10.0 |
| Polybutene 30 CST | 4.0 |
| Ethylhexyl p-methoxycinnamate | 4.0 |
| Ethylcellulose STD 100 | 1.0 |
| Isobutane | 25.0 |
| Propane | 5.0 |
| | 100.0 |

EXAMPLE 6

| INGREDIENTS | PERCENT BY WEIGHT |
| --- | --- |
| Ethanol | 38.5 |
| Padimate O | 8.0 |
| 2-Ethylhexyl salicylate | 3.0 |
| Ethylhexyl p-methoxycinnamate | 5.0 |
| Dimethylpolysiloxane 50 est. | 1.0 |
| Methyl phenyl polysiloxane | 3.0 |
| Ethylcellulose STD 100 | 1.0 |
| Isobutane | 25.0 |
| Propane | 5.0 |
| $C_{12}$–$C_{14}$ isoparaffin | 10.0 |
| Fragrance | 0.5 |
| | 100.0 |

EXAMPLE 7

| Ingredients | PERCENT BY WEIGHT |
| --- | --- |
| Benzyl alcohol | 10.0 |
| Ethanol | 36.5 |
| Padimate O | 8.0 |
| Ethyl 4-bis(hydroxypropyl) aminobenzoate | 5.0 |
| Dimethylpolysiloxane 50 cst. | 1.0 |
| Methyl phenyl polysiloxane | 3.0 |
| Ethylcellulose STD 100 | 1.0 |
| Dimethyl succinate | 5.0 |
| Isobutane | 25.0 |
| Propane | 5.0 |
| Fragrance | 0.5 |
| | 100.0 |

What I claim is:

1. An aerosol water-proof sunscreen composition comprising:

A. from about 20% to about 90% by weight of a monohydric alcohol;
B. from about 0.1% to about 5.0% by weight of ethylcellulose polymer having an average ethoxyl substitution from about 2.20 to about 2.65 and an ethoxyl content from about 44.8% to about 52.2%;
C. from about 1.0% to about 20.0% by weight of an active ultraviolet radiation absorber; and
D. from about 10% to about 7.5% by weight of a liquified propellant.

2. An aerosol water-proof sunscreen composition according to claim 1 wherein said ultraviolet radiation absorbers are selected from a group consisting of para-aminobenzoic acid; 2-ethoxyethyl p-methoxycinnamate; diethanolamine p-methoxycinnamate; digalloyl trioleate; 2,2'-dihydroxy-4-methoxybenzophenone; ethyl 4-(bis(hydroxypropyl))aminobenzoate; 2-ethylyhexyl salicylate; glyceryl aminobenzoate; 3,3,5-trimethylcyclohexyl salicylate; 2-ethylhexyl 2-cyano-3,3-diphenylacrylate; ethylhexyl p-methoxycinnamate; menthyl o-aminobenzoate; 2-hydroxy-4-methoxybenzophenone; amyl p-dimethylaminobenzoate; octyl p-dimethylaminobenxoate; 2-phenylbenzimidazole-5 sulfonic acid; 5-benzoyl-4-hydroxy-2-methoxybenzone-sulfonic acid); triethanolamine salicylate; 4-tert.butyl-4-methoxy-dibenzoylmethane; and benzalphthalide.

3. An aerosol water-proof sunscreen composition according to claim 1 wherein said liquified propellant is selected from the group consisting of butane; isobutane; propane; dimethyl ether; dichlorodifluoromethane; tetrafluoromethane; dichlorotetrafluoroethane; chlorodifluoromethane; chlorodifluoroethane; and difluoroethane.

4. An aerosol water-proof sunscreen composition according to claim 1 which additionally comprises:
   a. from about 0% to about 35% by weight of a volatile liquid carrier, having a melting point less than 22 degrees C. which completely evaporates from the skin after thirty minutes after application to the skin selected from the group consisting of hydrocarbons; halogenated hydrocarbons; and esters;
   b. from about 0% to about 20% by weight of a water-insoluble liquid, organic emollient compound having a water-solubility of less than 1% at 25 degrees C. selected from a group consisting of fatty alcohols, fatty acids, esters, ethers, alkanes, alkenes, and polysiloxanes; and
   c. from about 0% to about 3% by weight of a fragrance oil.

5. An aerosol water-proof sunscreen composition according to claim 4 wherein
   a. said monohydric alcohol is selected from the group consisting of ethanol and isopropanol;
   b. said active ultraviolet radiation absorber is selected from a group consisting of para-aminobenzoic acid; 2-ethoxyethyl p-methoxycinnamate; diethanolamine p-methoxycinnamate; digalloyl trioleate; 2,2'-dihydroxy-4-methoxybenzophenone; ethyl 4-[bis(hydroxypropyl)]aminobenzoate; 2-ethylyhexyl salicylate; glyceryl aminobenzoate; 2-cyano-3; 3-diphenylacrylate; ethylhexyl p-methoxycinnamate 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5 sulfonic acid; (5-benzoyl-4-hydroxy-2-methoxybenzone-sulfonic acid); triethanolamine salicylate; 4-tert-butyl-4'-methoxy-dibenzylmethane; and benzalphthalide;
   c. said liquified propellant is selected from a group consisting of butane; isobutane; propane; dimethyl ether; dichlorodifluoromethane; tetrafluoromethane; dichlorotetrafluoroethane; chlorodifluoromethane; chlorodifluoroethane; and difluoroethane;
   d. said volatile liquid carrier is selected from a group consisting of dimethyl succinate, trichlorofluoromethane, and $C_{10}$–$C_{16}$ isoparaffins; and
   e. said liquid emollient is selected from a group consisting of oleic acid, lauryl alcohol, di-isopropyl adipate, mineral oils, polybutene, dimethylpolysiloxane, polyoxypropylene butyl ether and methyl phenyl polysiloxane.

6. An aerosol water-proof sunscreen composition having an active ultraviolet radiation absorber comprising:
   A. from about 0.5% to about 2.0% by weight of an ethylcellulose polymer having an ethoxyl content from about 46.5% to about 50.0% and a viscosity polymer molecule designation from about 4 to about 200;
   B. from about 25% to about 65% by weight of a monohydric alcohol selected from a group consisting of ethanol isopropanol, and benzyl alcohol;
   C. from about 2% to about 16% by weight of an active ultraviolet radiation absorber selected from a group consisting of para-aminobenzoic acid; 2-ethoxyethyl p-methoxycinnamate; diethanolamine p-methoxycinnamate; digalloyl trioleate; 2,2'-dihydroxy-4-methoxybenzophenone; ethyl 4-(bis(hydroxypropyl))aminobenzoate; 2-ethylhexyl salicylate; glyceryl aminobenzoate; 2-cyano-3, 3-diphenylacrylate; ethylhexyl p-methoxcinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5 sulfonic acid; 5-benzoyl-4-hydroxy-2-methoxybenzone-sulfonic acid); triethanolamine salicylate; 4-tert-butyl-4'- methoxy-dibenzylmethane; and benzalphthalide;
   D. from about 20% to about 50% by weight of a liquified propellant selected from a group consisting of butane; isobutane; propane; dimethyl ether; dichlorodifluoromethane; tetrafluoromethane; dichlorotetrafluoroethane; chlorodifluoromethane; chlorodifluoroethane; and difluoroethane;
   E. from about 5% to about 20% by weight of a volatile liquid carrier selected from a group consisting of dimethyl succinate, trichlorofluoromethane, $C_{10}$–$C_{16}$ and isoparaffins; and
   F. from about 2% to about 10% by weight of a water-insoluble liquid emollient selected from a group consisting of oleic acid, lauryl alcohol, di-isopropyl adipate, mineral oils, polybutene, dimethylpolysiloxane, polyoxypropylene butyl ether and methyl phenyl polysiloxane.

7. An aerosol water-proof sunscreen composition according to claim 6 wherein the monohydric alcohol is ethanol.

8. An aerosol water-proof sunscreen composition according to claim 6 wherein the active ultraviolet radiation absorber is octyl p-dimethylaminobenzoate.

9. An aerosol water-proof sunscreen composition according to claim 6 wherein the active ultraviolet radiation absorber is 2,2'-dihydroxy-4-methoxybenzophenone.

10. An aerosol water-proof sunscreen composition according to claim 6 wherein the active ultraviolet radiation absorber is 2-hydroxy-4-methoxybenzophenone Oxybenzone.

11. An aerosol water-proof sunscreen composition according to claim 6 wherein the active ultraviolet radiation absorber is ethyl 4-bis-(hydroxypropyl)aminobenzoate.

12. An aerosol water-proof sunscreen composition according to claim 6 wherein the active ultraviolet radiation absorber is ethyl p-methoxycinnamate.

13. An aerosol water-proof sunscreen composition according to claim 6 wherein the active ultraviolet radiation absorber is octyl p-dimethylaminobenzoate and 2,2'-dihydroxy-4-methoxybenzophenone.

14. An aerosol water-proof sunscreen composition according to claim 6 wherein the ethylcellulose polymer is an ethylcellulose having an ethoxyl substitution between 48.0% to 49.55.

15. An aerosol water-proof sunscreen composition according to claim 6 wherein the propellant comprises isobutane and propane.

16. An aerosol water-proof sunscreen composition according to claim 6 wherein the volatile liquid carrier is $C_{12}$–$C_{14}$ isoparaffin.

17. An aerosol water-proof sunscreen composition according to claim 6 wherein the volatile liquid carrier is dimethyl succinate.

18. An aerosol water-proof sunscreen composition according to claim 6 wherein the water insoluble liquid emollient is polybutene 30 cst.

19. An aerosol water-proof sunscreen composition according to claim 6 wherein the water insoluble liquid emollient is dimethylpolysiloxane 50 cst.

20. An aerosol water-proof sunscreen composition according to claim 6 wherein the water insoluble liquid emollient is polyoyxpropylene (14) butyl ether.

21. An aerosol water proof sunscreen composition according to claim 6 wherein the water insoluble liquid emollient is methyl phenyl siloxane.

* * * * *

UNITED STATES PATENT AND TRADEMARK OFFICE
CERTIFICATE OF CORRECTION

PATENT NO. : 4,686,099

DATED : August 11, 1987

INVENTOR(S) : Victor Palinczar

It is certified that error appears in the above-identified patent and that said Letters Patent is hereby corrected as shown below:

In the Claims:

Claim 1, Paragraph D, line 1; delete "7.5%" and insert therefor --75%--.

Claim 10, line 4; delete "Oxybenzone".

Signed and Sealed this

Twenty-ninth Day of March, 1988

Attest:

DONALD J. QUIGG

*Attesting Officer*    *Commissioner of Patents and Trademarks*